(12) United States Patent
Motosugi

(10) Patent No.: US 8,167,893 B2
(45) Date of Patent: May 1, 2012

(54) ENDOSCOPIC TREATMENT INSTRUMENT

(75) Inventor: Shunsuke Motosugi, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 562 days.

(21) Appl. No.: 11/903,116

(22) Filed: Sep. 20, 2007

(65) Prior Publication Data

US 2008/0215064 A1   Sep. 4, 2008

(30) Foreign Application Priority Data

Sep. 22, 2006   (JP) ................ P2006-257351

(51) Int. Cl.
*A61B 17/00*   (2006.01)
(52) U.S. Cl. .............. 606/113; 600/104; 600/127
(58) Field of Classification Search .............. 600/47, 600/104, 106, 114, 117, 127, 153; 606/110, 606/113, 114, 127
See application file for complete search history.

(56) References Cited

U.S. PATENT DOCUMENTS

| | | | | |
|---|---|---|---|---|
| 5,487,757 | A * | 1/1996 | Truckai et al. | 604/264 |
| 2004/0158124 | A1 | 8/2004 | Okada | |
| 2004/0158127 | A1 | 8/2004 | Okada | |
| 2005/0033115 | A1* | 2/2005 | Okada | 600/104 |

FOREIGN PATENT DOCUMENTS

| | | |
|---|---|---|
| DE | 101 26 062 A1 | 12/2001 |
| DE | 103 56 018 A1 | 7/2004 |
| JP | 2002-045369 | 2/2002 |
| JP | 2004-230054 | 8/2004 |
| JP | 2005-058343 A | 3/2005 |
| JP | 2005-103140 A | 4/2005 |

OTHER PUBLICATIONS

Japanese Office Action dated Aug. 23, 2011 from corresponding Japanese Patent Application Publication No. 2006-257351 together with partial English language translation.

* cited by examiner

*Primary Examiner* — Ryan Severson
*Assistant Examiner* — Ashley Cronin
(74) *Attorney, Agent, or Firm* — Scully, Scott, Murphy & Presser, P.C.

(57) ABSTRACT

An endoscopic treatment instrument is provided comprising: a cylinder adapted to be fitted over a tip of an insertion section of an endoscope; a loop-shaped snare wire which protrudes in the cylinder from a snare sheath that is extendable and retractable with respect to the insertion section and which is extendable within the cylinder; a hooked portion which is formed and radially inwardly extended from the circumference of the tip of cylinder and which holds the snare wire within the cylinder; a locking portion which is provided on the hooked portion and retains a folded-back portion of the snare wire that is forwardly moved toward the cylinder tip with respect to the snare sheath and by means of which the snare wire is turned upside-down around the folded-back portion.

5 Claims, 15 Drawing Sheets

ENDOSCOPIC TREATMENT INSTRUMENT

BACKGROUND OF THE INVENTION

1. Field of the Invention

The present invention relates to an endoscopic treatment instrument. Priority is claimed on Japanese Patent Application No. 2006-257351, filed Sep. 22, 2006, the content of which is incorporated herein by reference.

2. Description of the Related Art

With respect to early-stage cancer of the stomach or esophagus, an endoscopic demucosation is performed in which a mucosa in an ailing or affected area is excised by using a frequency snare introduced into a body cavity through a channel of the endoscope. In such a demucosational operation, an endoscopic treatment instrument is used which includes a generally cylindrical transparent cap that is fitted over the tip of an insertion section of the endoscope.

In an operation with the use of this endoscopic treatment instrument, a snare wire of the high frequency snare is firstly extended radially in the transparent cap and then a mucosa to be excised is absorbed so as to form the shape of a polyp in the transparent cap while the snare wire is extended as it is. Thereafter, a base portion of the polyp-shaped mucosa is excised by the use of the frequency snare. At this time, it is necessary for the snare wire to be precisely placed on the base portion of the polyp-shaped mucosa drawn in the transparent cap. To this end, there is a proposal in which a hooked portion is provided on the tip of the transparent cap and the snare wire is extended along the hooked portion and retained as it is. See, e.g., Japanese Unexamined Patent Application, First Publication Nos. 2002-45369 and 2004-230054.

With the above-described conventional endoscopic treatment instrument, it is impossible to extend the snare wire in the transparent cap while maintaining the transparent cap in a floating state or so as to be untouched. Namely, when the snare wire is extended, the transparent cap is inevitably pressed against tissues or mucosa. As such, the transparent cap is firstly pressed against a normal area or tissue and the snare wire is then projected through a treatment tool insertion channel. At this time, the affected area necessarily goes out of view of the endoscope. So, it takes a lot of time and trouble to find the affected area again for excising the polyp thereof. Furthermore, a lot of skill is necessary to speed up a pre-looping operation in which the snare wire is extended (or a loop of the snare wire is widened) in the transparent cap. Furthermore, since the snare wire is forwardly and rearwardly moved through the treatment tool insertion channel of the insertion section, it is necessary to pull out the treatment tool concerned in order to replace it with another treatment tool such as an injection needle and the like.

SUMMARY OF THE INVENTION

In light of the circumstances, the present invention has been made and has an aim of providing a endoscopic treatment instrument in which, even when the cylinder or cap is floating or cantilevered, it is possible to extend (or widen the loop of) the snare wire in the cylinder.

In order to attain the above object, the present invention employs the following means. According to the present invention, an endoscopic treatment instrument is provided comprising: a cylinder adapted to be fitted over a tip of an insertion section of an endoscope; a loop-shaped snare wire which protrudes in the cylinder from a snare sheath that is extendable and retractable with respect to the insertion section and which is extendable within the cylinder; a hooked portion which is formed and radially inwardly extended from the circumference of the tip of cylinder and which holds the snare wire within the cylinder; a locking portion which is provided on the hooked portion and retains a folded-back portion of the snare wire that is forwardly moved toward the cylinder tip with respect to the snare sheath and by means of which the snare wire is turned upside-down around the folded-back portion.

According to the present invention, due to the existence of the locking portion, it is possible to make the folded-back portion of the snare wire protruding through the snare sheath abut against the hooked portion 3 such that the folded-back portion is locked or hooked. At this time, by forwardly moving the snare wire with respect to the snare sheath to thereby generate compression force in the snare wire, it is possible to develop the loop of the snare wire along the hooked portion with the folded-back portion functioning as a base point.

Preferably, the locking portion is disposed at a front side in a protruding direction of the snare wire with respect to the snare sheath.

According to the present invention, by simply making the snare wire protrude through the snare sheath, it is possible for the folded-back portion of the snare wire to abut against the locking portion.

Preferably, the locking portion includes an auxiliary hooked portion which protrudes from an end portion, in the vicinity of which the extension of the snare wire intersects, of the hooked portion toward a base end side of the cylinder.

According to the present invention, it is possible to make the folded-back portion of the snare wire abut against the hooked portion and to block the forward movement of the folded-back portion of the snare wire by the auxiliary hooked portion.

Preferably, the locking portion includes a depressed portion or through-hole which is provided on the hooked portion in the vicinity of which the extension of the snare wire intersects.

According to the present invention, it is possible to appropriately hook the folded-back portion at the depressed portion or the through-hole and turn the snare wire upside-down with respect to the hooked portion.

Preferably, the locking portion includes a friction generating portion which is provided on an outer surface of the hooked portion and which has a larger coefficient of friction than the outer surface of the hooked portion.

According to the present invention, it is possible to hook the folded-back portion due to high friction force generated by the friction generating portion and to extend the snare wire with the folded-back portion as it is.

Preferably, the endoscopic treatment instrument further comprises a tube which opens at its tip in the cylinder and in which the snare sheath is received so as to be extendable and retractable.

According to the present invention, by inserting the snare sheath into the tube, it is possible to insert a treatment tool other than the snare wire into the treatment tool insertion channel of the insertion section of the endoscope. Thus, it is possible to decrease the number of taking-out and putting-in operations of the frequency snare at the time of using a plurality of different treatment tools.

According to the present invention, it is possible to extend the snare wire in the cylinder while maintaining the cylinder in a floating state or so as to be untouched.

DETAILED DESCRIPTION OF THE INVENTION

Hereinafter, preferred embodiments of the present invention will be described with reference to the drawings. However, it should not be construed that the present invention is limited to these embodiments, but rather, components of these embodiments may be combined if necessary.

Referring now to FIGS. 1 to 10, a description will be given of a first embodiment according to the present invention.

Figure 5:
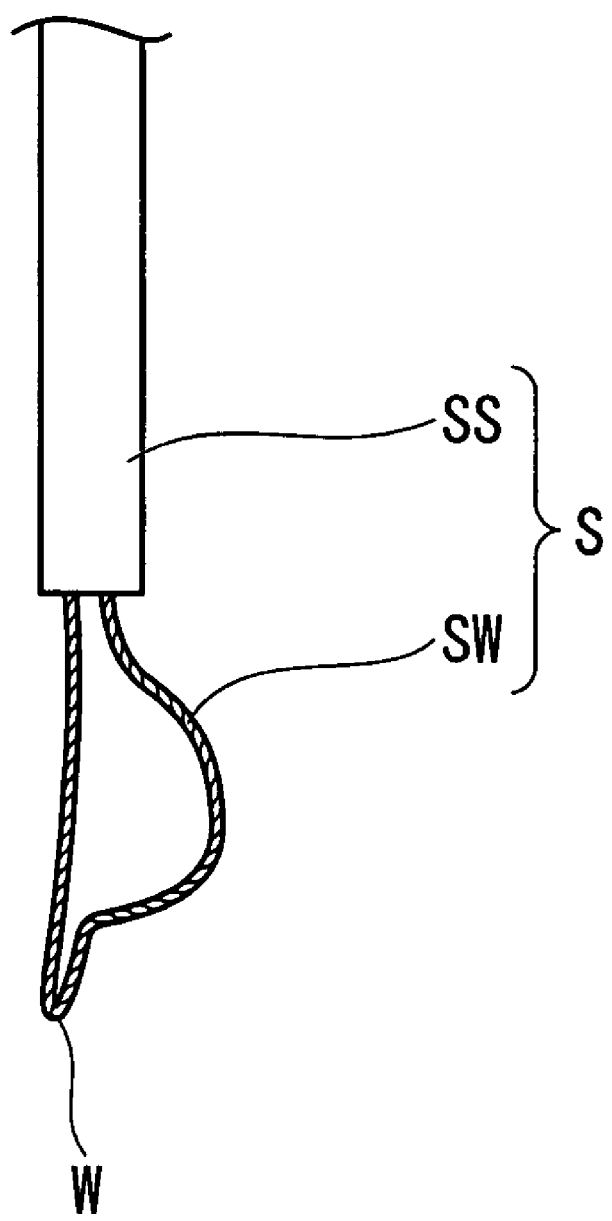
FIG. 5 is a plan view illustrating a high frequency snare that is used together with the endoscope hood according to the first embodiment of the present invention.

As illustrated in FIGS. 1 to 4, an endoscope hood (endoscopic treatment instrument) 1 is provided with a transparent cylindrical cap portion (cylinder) 2 the proximal end of which is fitted on the tip of an insertion section I1 of an endoscope E1 via a fitting portion 7 (described later). As illustrated in FIG. 5, a high frequency snare S is forwardly and rearwardly movable with respect to the insertion section I1 and includes a snare sheath SS and a snare wire SW which is protrudable in a meniscus or looped shape through the snare sheath SS. The endoscope hood 1 is used when the snare wire SW is projected into the cap portion 2 and then radially extended.

The endoscope hood 1 is provided with a hooked portion 3 which is radially inwardly extended from the circumference of the tip of the cap portion 2 and which retains within the inside of the cap portion 2 the loop-shaped snare wire SW in an extended manner, with a locking portion 5 which is formed on the hooked portion 3 and which swingably catches a folded-back portion W of the tip of the snare wire SW that is forwardly moved toward the tip of the cap portion 2 with respect to the snare sheath SS, and with a flexible tube (pipe portion) 6 which has a frontal end opened within the cap portion 2 and in which the snare sheath SS is extendably and retractably received.

At the proximal end side, a protruding portion 2A is provided which controls insertion of the insertion portion I1 of the endoscope E1 within the cap portion 2. The cylindrical fitting portion 7 is provided so that the cap portion 2 is detachably secured to the tip of the insertion portion I1. The fitting portion 7 and the cap portion 2 are connected with a common center axis C. The flexible tube 6 has a center axis C1 which is separately disposed parallel to the center axis C. The cap portion 2 includes a tip end aperture plane 2a that is formed and slanted at a predetermined angle with respect to the center axis C of the cap portion 2 such that the length from the proximal end of the cap portion 2 to an intersecting point between the tip end aperture plane 2a and the center axis C1 of the flexible tube 6 is shorter than any other corresponding length.

The hooked portion 3 is formed along the tip end aperture plane 2a and has a length so as to prevent the snare wire SW from protruding when the snare wire SW is extended in the cap portion 2.

The locking portion 5 is provided with an auxiliary hooked portion 8 that is formed by being bent at an end part, in the vicinity of an intersecting point between the hooked portion 3 and the center axis C1 of the flexible tube 6, of the hooked portion 3 and by being extended toward the proximal end of the cap portion 2. The auxiliary hooked portion 8 and the hooked portion 3 may be integrally formed in one piece or may be separately formed and then assembled.

Figure 1:
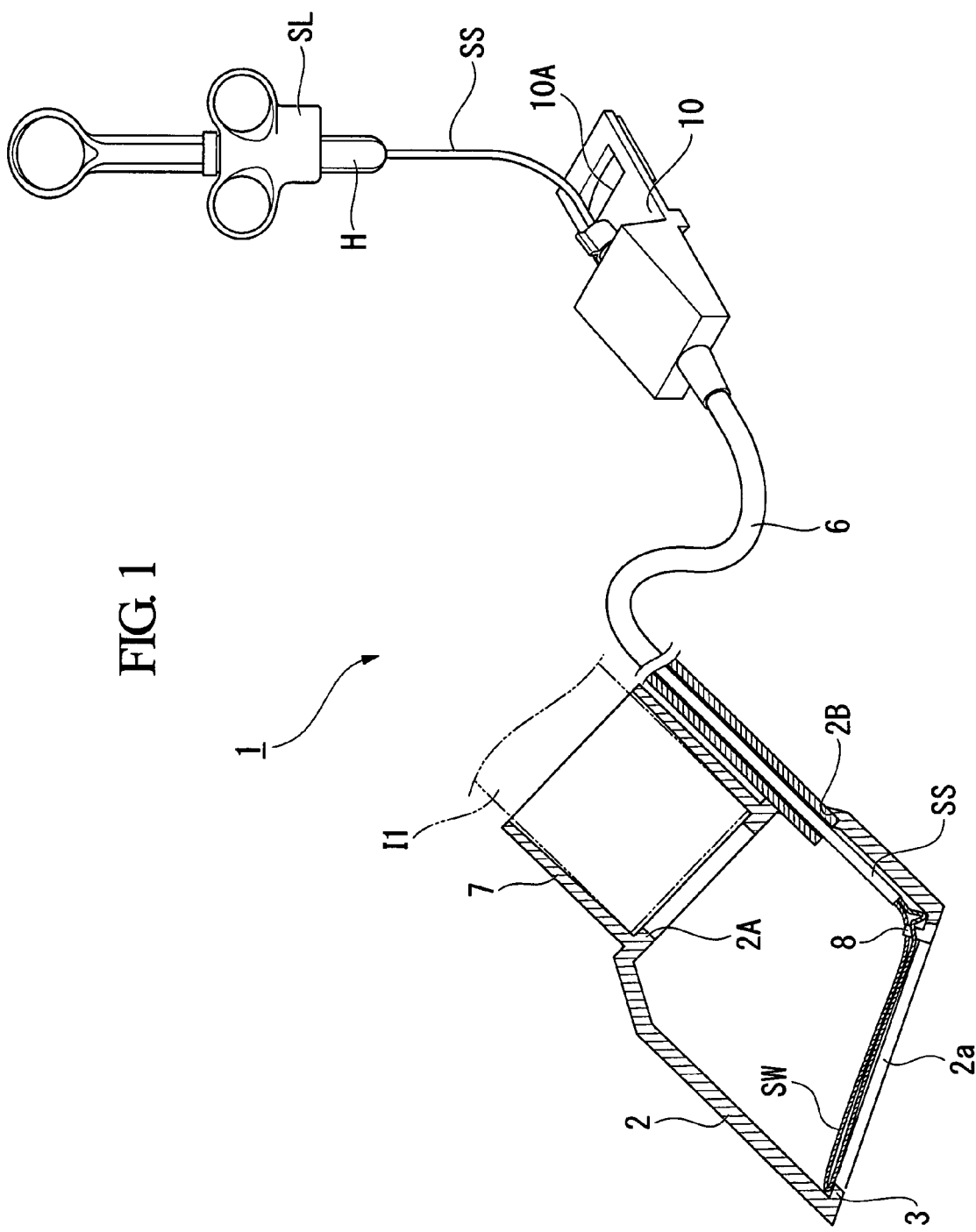
FIG. 1 is a general schematic view illustrating an endoscope hood according to a first embodiment of the present invention.
Figure 2:
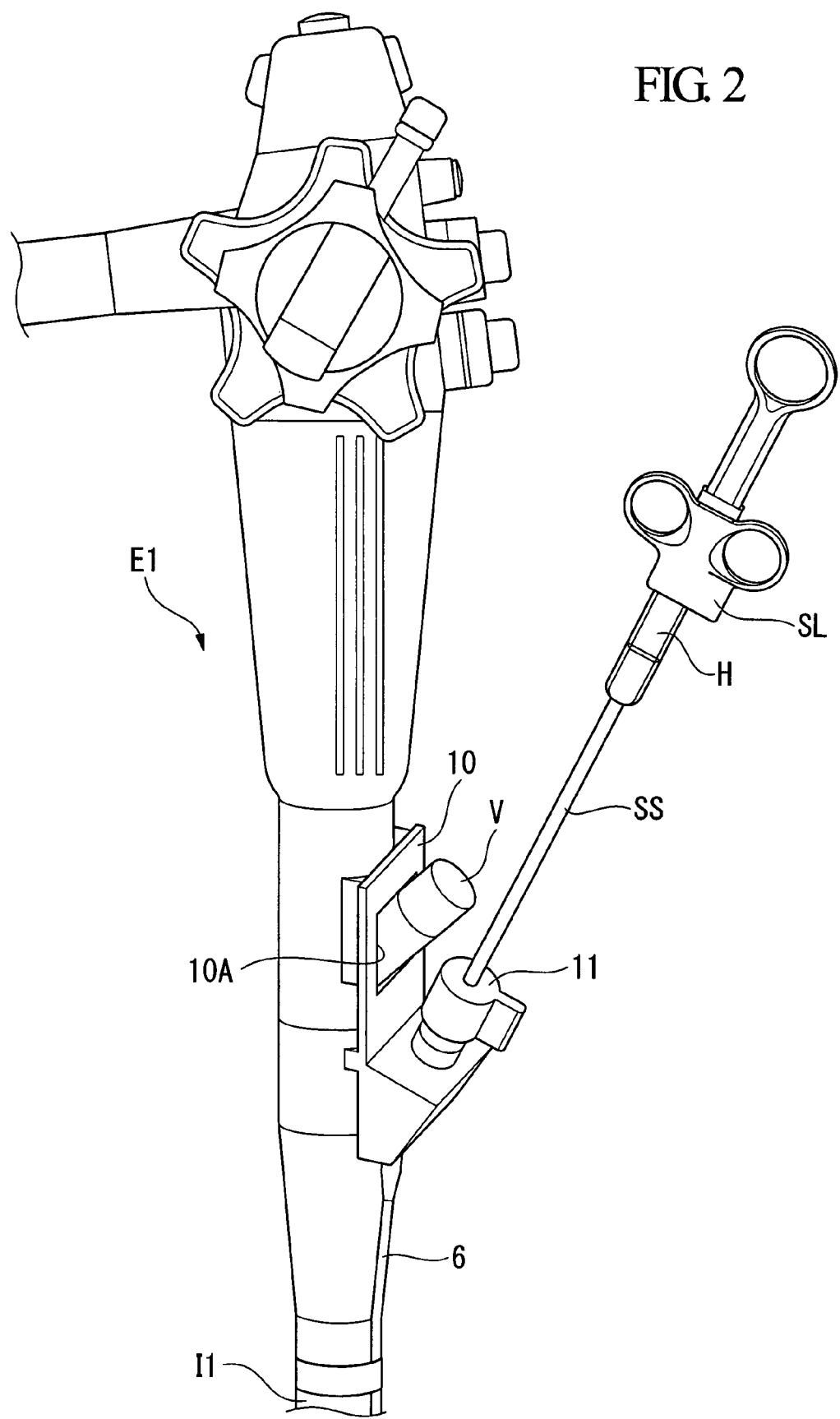
FIG. 2 is a schematic view illustrating an endoscope on which the endoscope hood according to the first embodiment of the present invention is mounted.

The flexible tube 6 is connected into a communication hole 2B which is formed on the side of the cap portion 2, so that it communicates with the inside of the cap portion 2. The flexible tube 6 has substantially the same length as the insertion section I1 and has a proximal end to which an attaching section 10 that is suspended by and fixed to a forceps opening V of the endoscope E1 is connected, as illustrated in FIG. 1. The attaching section 10 is provided with a hook hole 10A into which the forceps opening V is insertable. The attaching section 10 is also provided with an air-tight valve (gas-tight valve) 11 into which the snare sheath SS is inserted.

A control portion main body H is provided on the proximal end of the snare sheath SS. A slider SL is connected to the proximal end of the snare wire SW such that it is advanceable and retractable with respect to the control portion main body H.

Next, with further reference to FIGS. 6 to 10, a description will be given of the operation of the endoscope hood 1 according to the present embodiment. Here, the following is a sequence or procedure of cutting an unillustrated mucosa (endoscopic demucosation) by the use of the endoscope E1 with the endoscope hood 1 fitted thereon.

Firstly, the fitting portion 7 of the endoscope hood 1 is fitted over the tip of the insertion section I1 of the endoscope E1, and then, the flexible tube 6 is fixedly secured along the insertion section I1 by the use of tape for medical use. The thus-conditioned insertion section I1 is inserted in a body cavity, and then, the tip end aperture plane 2a of the cap portion 2 is positioned in the vicinity of a mucosa portion to be excised while it is being observed.

Figure 3:
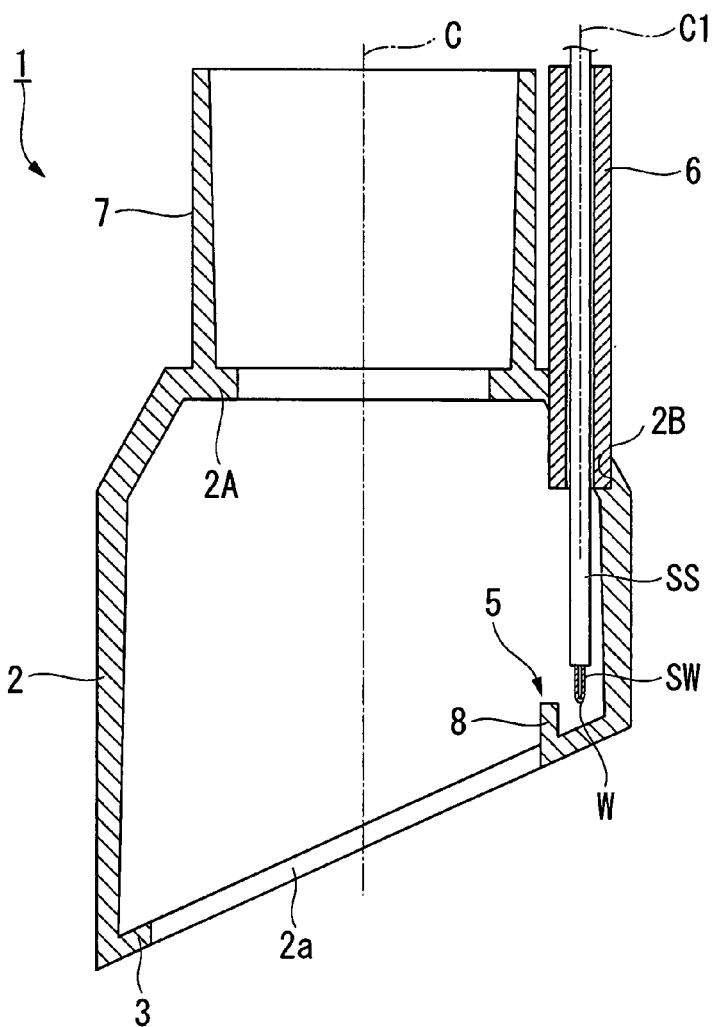
FIG. 3 is a cross-sectional view illustrating a main portion of the endoscope hood according to the first embodiment of the present invention.
Figure 4:
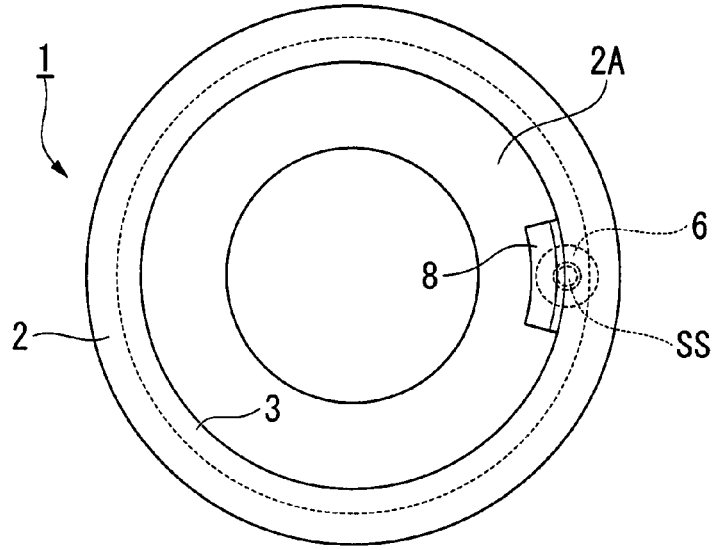
FIG. 4 is a frontal view of the endoscope hood according to the first embodiment of the present invention.
Figure 6:
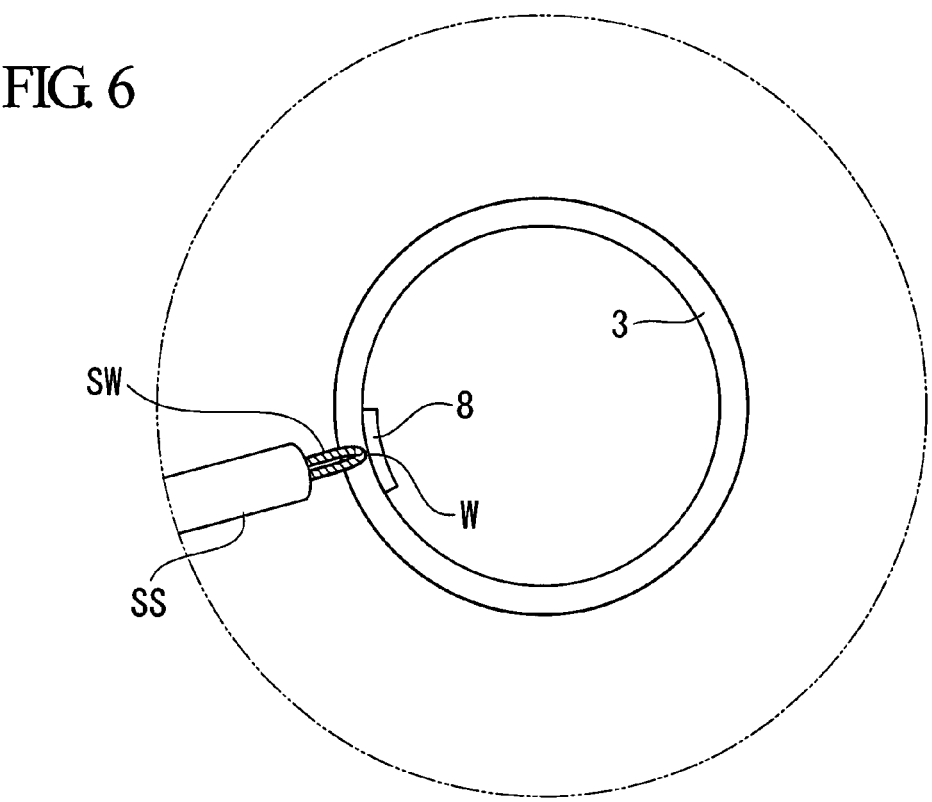
FIG. 6 is a view illustrating an operational state of the endoscope hood according to the first embodiment of the present invention when viewed from the endoscope side.

Subsequently, the snare sheath SS is inserted through the air-tight valve 11 into the flexible tube 6 until the tip thereof protrudes into the inside of the cap portion 2. Thereafter, the slider SL is forwardly moved or advanced with respect to the control portion main body H, so that the folded-back portion W of the snare wire SW protrudes from the snare sheath SS, as illustrated in FIG. 3, and then abuts against the hooked portion 3 and hence engages the auxiliary hooked portion 8, as illustrated in FIG. 6.

Figure 7:
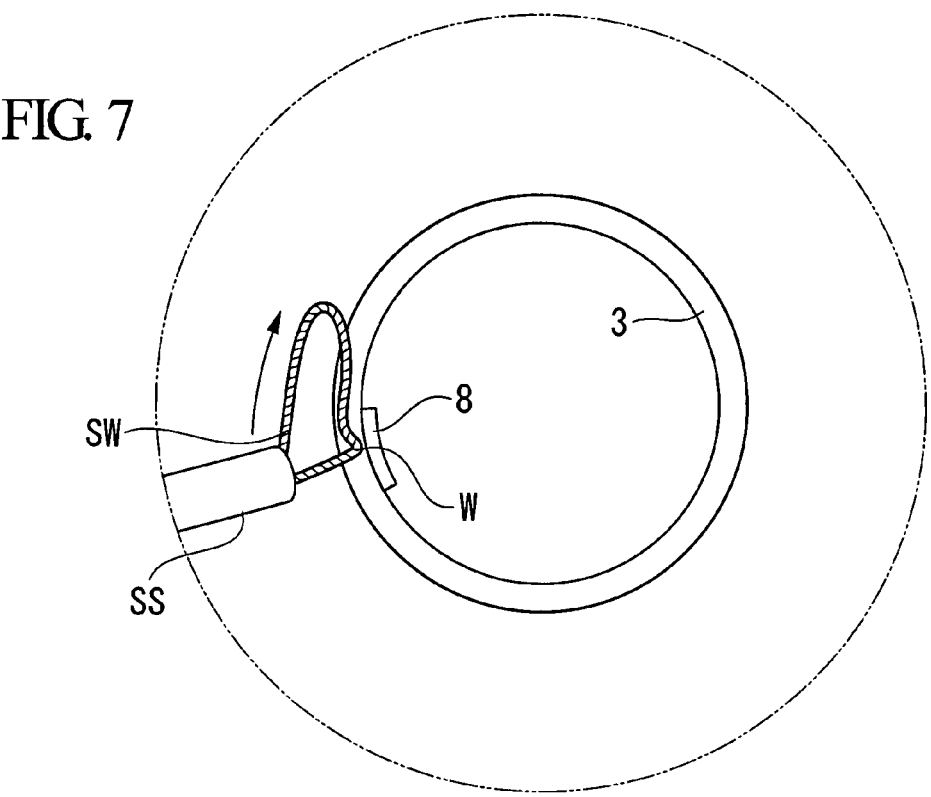
FIG. 7 is a view illustrating a further operational state of the endoscope hood according to the first embodiment of the present invention when viewed from the endoscope side.
Figure 8:
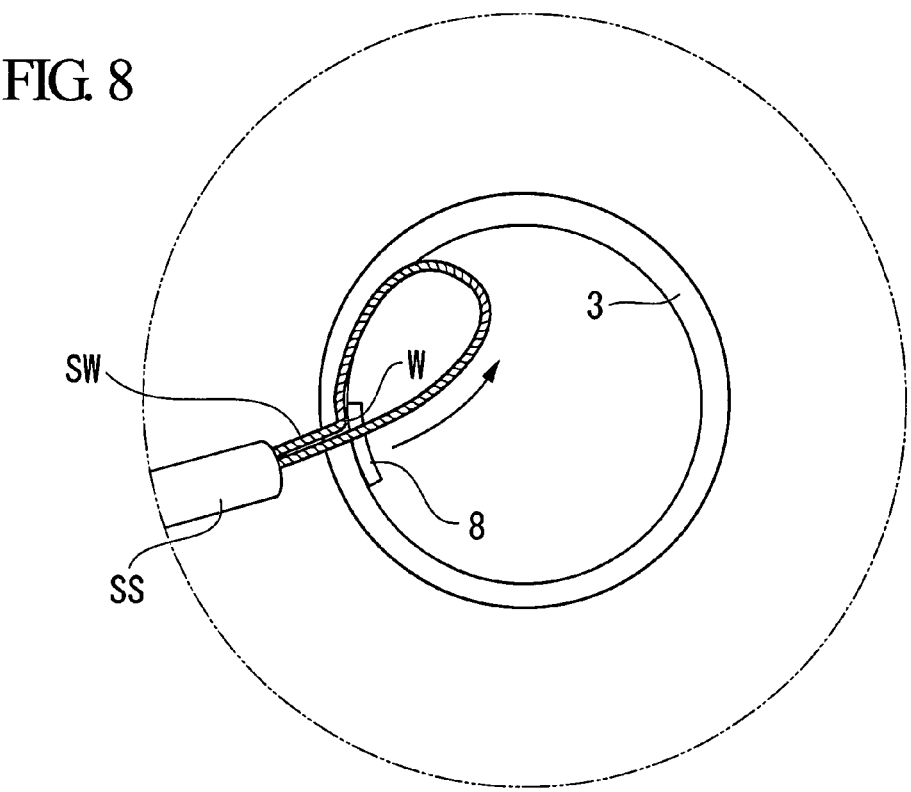
FIG. 8 is a view illustrating a yet further operational state of the endoscope hood according to the first embodiment of the present invention when viewed from the endoscope side.
Figure 9:
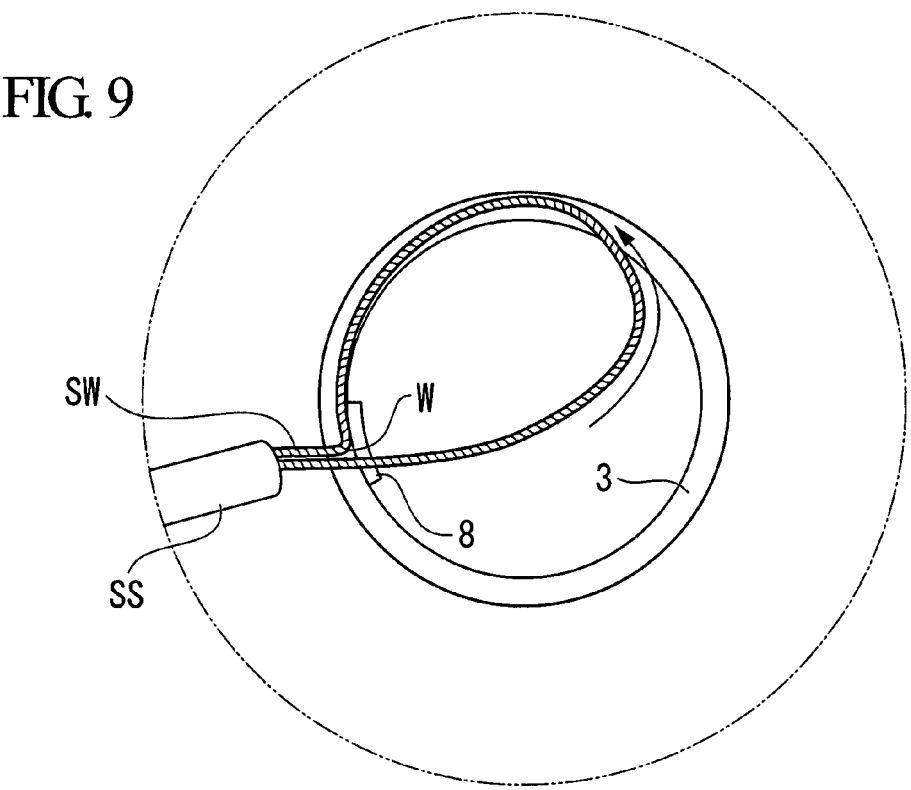
FIG. 9 is a view illustrating a still further operational state of the endoscope hood according to the first embodiment of the present invention when viewed from the endoscope side.
Figure 10:
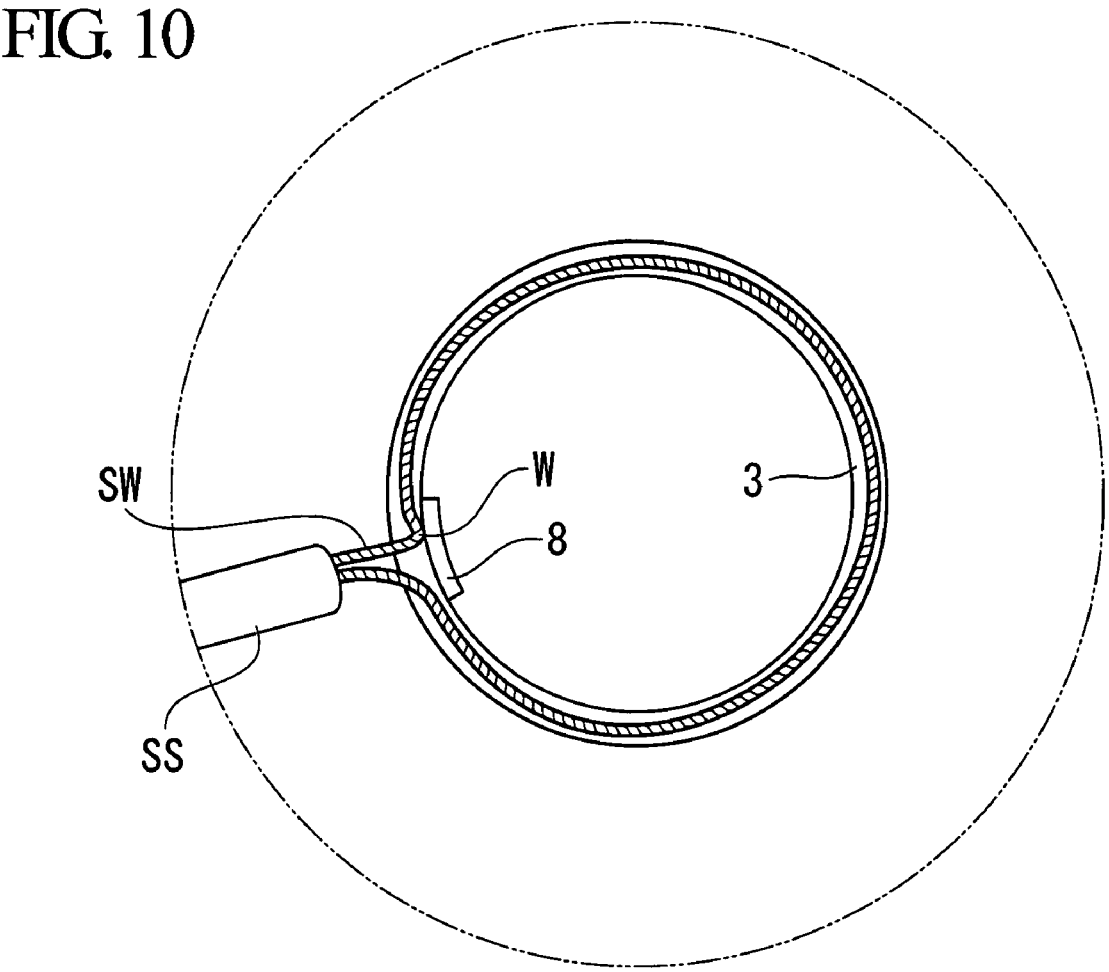
FIG. 10 is a view illustrating a different operational state of the endoscope hood according to the first embodiment of the present invention when viewed from the endoscope side.

Then, as illustrated in FIG. 7, when the folded-back portion W is hooked at the auxiliary hooked portion 8 and then the snare wire SW is further projected through the snare sheath SS, the folded-back portion W of the snare wire SW is retained as it is, and one side of the snare wire SW is only forwardly moved while swaying rightward and leftward. At this time, as illustrated in FIGS. 8 and 9, the movement of the other side of the snare wire SW, i.e., the folded-back portion W of the snare wire SW is blocked whereas the one side of the snare wire SW is moved along the hooked portion 3 such that the loop of the snare wire SW is widened in the cap portion 2. As illustrated in FIG. 10, the loop of the snare wire SW is finally formed extending throughout the circumference of the hooked portion 3.

In this state, an injection needle is extended through a treatment tool insertion channel (not shown) that is provided on the insertion section I1, into the inside of the cap portion 2 and then a physiological saline solution is injected for the swelling. Thereafter, the suction operation is carried out through the treatment tool insertion channel. Thus-suctioned (or drawn) mucous membrane is received in (the loop of) the snare wire SW that has been extended and then the binding and energizing operation relating to the snare wire is carried out by the use of the movement of the slider SL. Note that the swelling operation may be carried out by the use of the injection needle before the extension of the snare wire SW.

With this endoscope hood 1, due to the existence of the locking portion 5, it is possible to make the folded-back portion W of the snare wire SW protruding through the snare sheath SS abut against the hooked portion 3 and to block the forward movement of the folded-back portion of the snare wire SW in the cap portion 2 by the auxiliary hooked portion 8. At this time, by forwardly moving the snare wire SW with respect to the snare sheath SS to thereby generate compression force in the snare wire SW, it is possible to develop the loop of the snare wire SW along the hooked portion 3 with the folded-back portion W (which has been hooked to the locking portion 5) functioning as a base point. Therefore, it is possible to extend the snare wire SW in the cap portion 2 even when the cap portion 2 is in a floating state.

Further, by inserting the snare sheath SS into the flexible tube 6, it is possible to insert a treatment tool other than the snare wire SW into the treatment tool insertion channel of the insertion section I1 of the endoscope E1. Thus, it is possible to decrease the number of removal and insertion operations of the frequency snare S.

Figure 11:
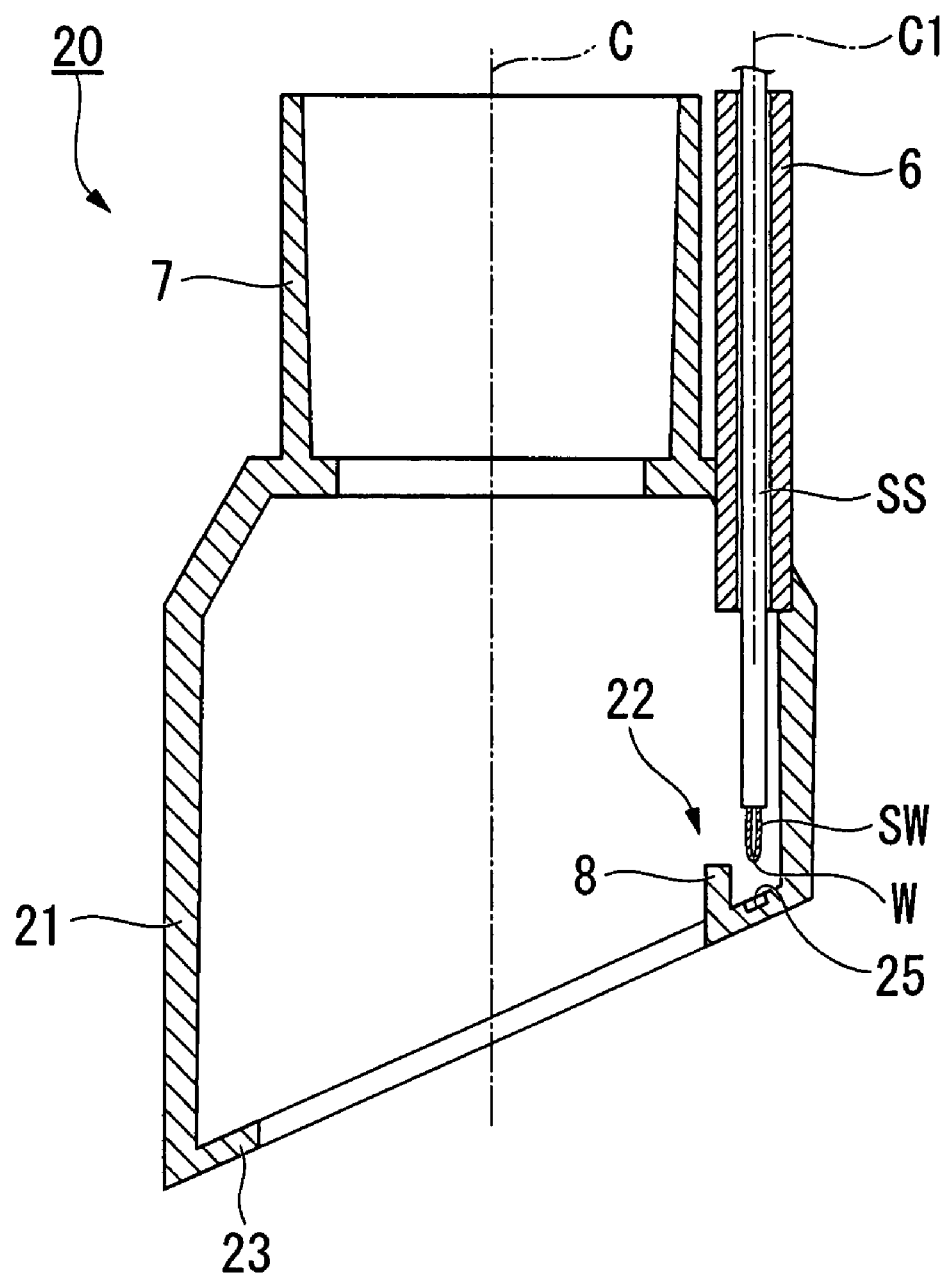
FIG. 11 is a cross-sectional view illustrating a main portion of an endoscope hood according to a second embodiment of the present invention.

Next, with reference to FIG. 11, a description will be given of a second embodiment of the present invention.

Note that components which are the same or equivalent as those of the above-mentioned first embodiment are assigned the same reference numerals and that duplicate descriptions are appropriately omitted.

The second embodiment is different from the first embodiment in that a locking portion 22 of a cap portion 21 of an endoscope hood 20 according to the second embodiment is provided with a depressed portion 25 formed in a hooked portion 23 in the vicinity of a position toward which the snare wire SW is advanced.

The depressed portion 25 is positioned at a position where the center axis C1 of the flexible tube 6 and the hooked portion 23 intersect. It is formed with a depth such that the folded-back portion W of the snare wire SW is partially insertable therein. Note that the present embodiment may be settled or completed without the auxiliary hooked portion 8.

Next, a description will be given of an operation of the endoscope hood 20 according to the second embodiment of the present invention.

Firstly, similarly to the first embodiment, the insertion portion I1 with the cap portion 21 fitted thereover is positioned or placed in the vicinity of a section which is to be cut from a mucosa. Subsequently, the tip of the snare sheath SS is projected in the cap portion 21 and the folded-back portion W of the snare wire SW is projected through the snare sheath SS. On this occasion, a part of the folded-back portion W of the snare wire SW is inserted and hooked in the depressed portion 25. Then, when the snare wire SW is projected through the snare sheath SS, the folded-back portion W of the snare wire SW is retained or held in the depressed portion 25 whereas one side portion of the snare wire SW only protrudes while swaying. In this way, the snare wire SW is extended in the cap portion 21 so as to follow the hooked portion 23 whereby a loop of the snare wire SW is formed extending throughout the circumference of the hooked portion 23.

With this endoscope hood 20, it is possible to obtain an operation and effects which are similar to those of the first embodiment. Specifically, since the locking portion 22 is provided with depressed portion 25 and since the folded-back portion W of the snare wire SW is engaged in the depressed portion 25, it is possible to appropriately hook the folded-back portion at the hooked portion 23 and turn the snare wire upside-down, as compared to a case in which the folded-back portion W is hooked at the auxiliary hooked portion 8.

Next, with reference to FIGS. 12 to 14, a description will be given of a third embodiment of the present invention.

Note that components which are the same or equivalent as those of the above-mentioned first and second embodiments are assigned the same reference numerals and that duplicate descriptions are appropriately omitted.

Figure 12:
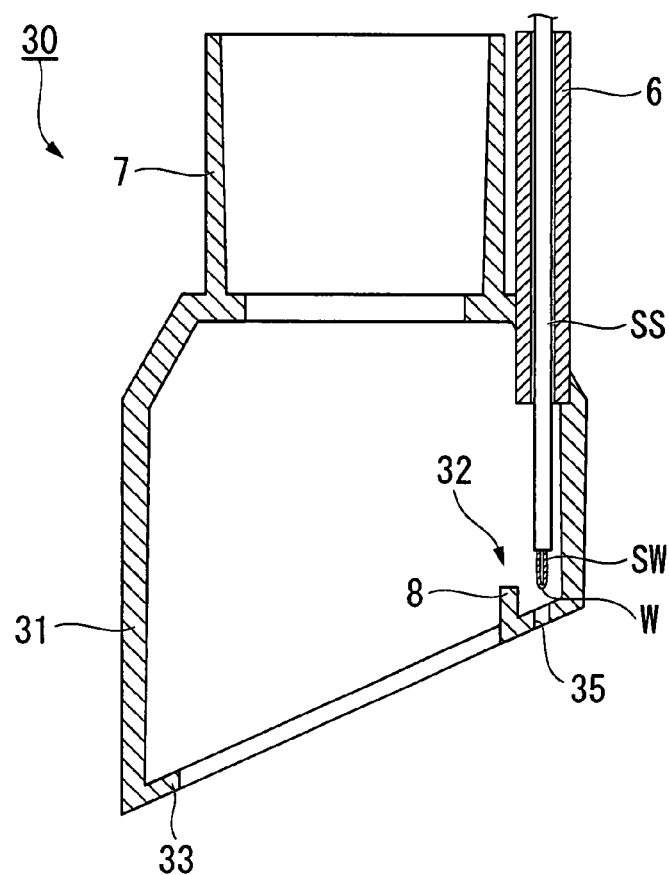
FIG. 12 is a cross-sectional view illustrating a main portion of an endoscope hood according to a third embodiment of the present invention.

The third embodiment is different from the second embodiment in that a locking portion 32 of a cap portion 31 of an endoscope hood 30 according to the third embodiment is provided with a through-hole 35, in stead of being provided with the depressed portion 25, which is formed in a hooked portion 33 and having a constant inside diameter as shown in FIG. 12. Note that the present embodiment may be settled or completed without the auxiliary hooked portion 8.

Figure 13:
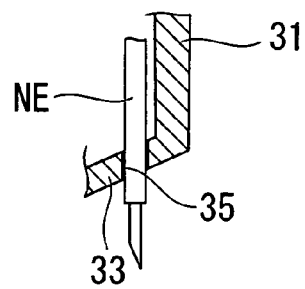
FIG. 13 is a partial cross-sectional view illustrating a state in which an injection needle is inserted through the endoscope hood according to the third embodiment of the present invention.
Figure 14:
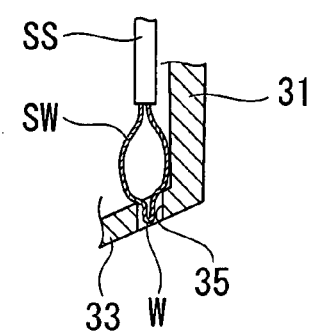
FIG. 14 is a partial cross-sectional view illustrating a state in which the high frequency snare is inserted in the endoscope hood according to the third embodiment of the present invention.

The through-hole 35 has a dimension such that the injection needle NE is insertable therethrough as shown in FIG. 13 and that the folded-back portion W of the snare wire SW is not insertable therethrough as shown in FIG. 14. This is intended for treating with the injection needle NE inserted through the flexible tube 6.

With this endoscope hood 30, it is possible to obtain an operation and effects which are similar to those of the second embodiment.

Figure 15:
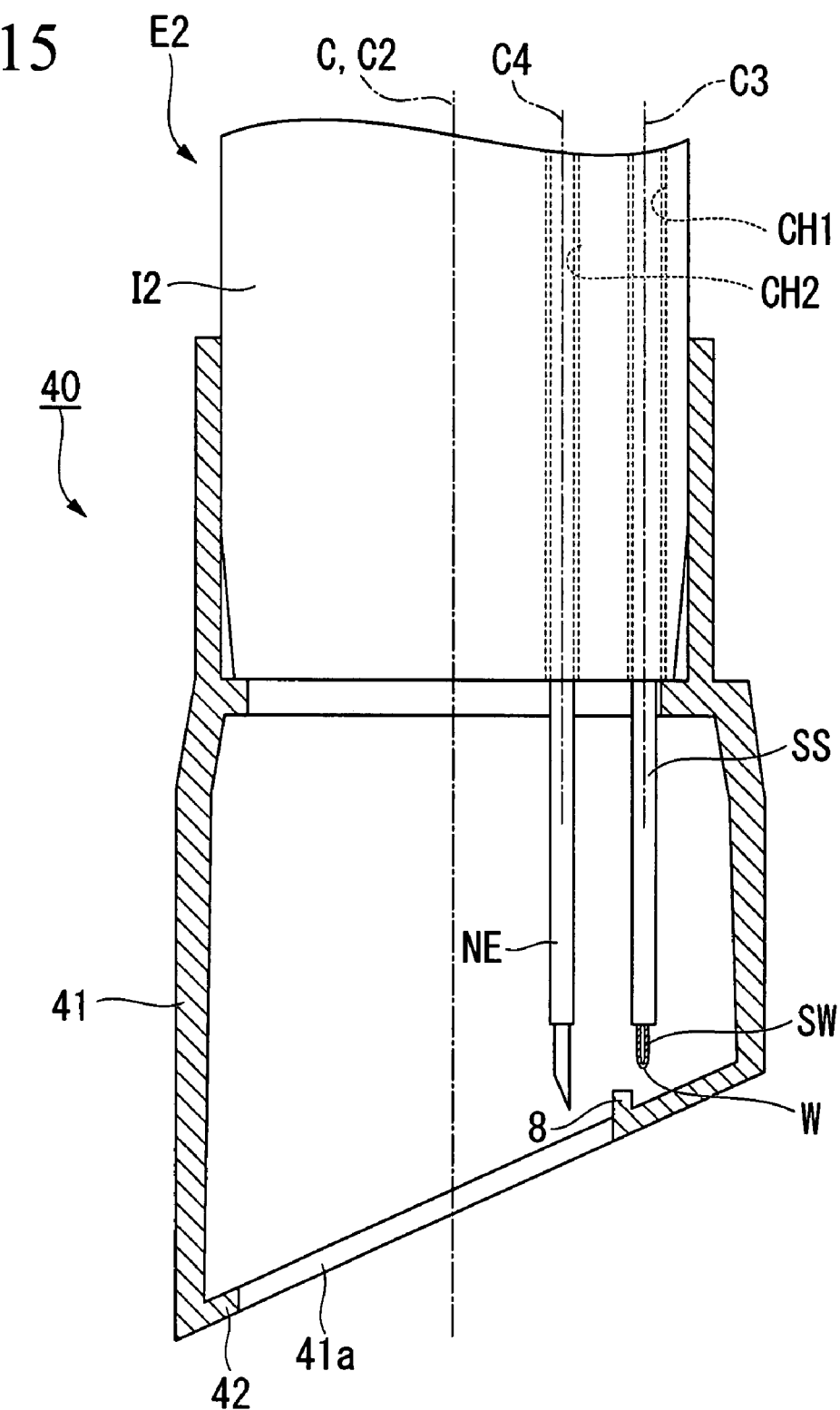
FIG. 15 is a cross-sectional view illustrating a main portion of an endoscope hood according to a fourth embodiment of the present invention.

Next, with reference to FIG. 15, a description will be given of a fourth embodiment of the present invention.

Note that components which are the same or equivalent as those of the above-mentioned first, second and third embodiments are assigned the same reference numerals and that duplicate descriptions are appropriately omitted.

The fourth embodiment is different from the first embodiment in that an endoscope hood 40 according to the fourth embodiment is not provided with the flexible tube 6. Namely, a cap portion 41 is not formed with a through-hole.

An insertion section I2, over which the cap portion 41 is fitted, of an endoscope E2 is provided with a first treatment tool insertion channel CH1 and a second treatment tool insertion channel CH2 which is disposed closer to a center axis C2 of the insertion section I2 than the first treatment tool insertion channel CH1 is. With this insertion section I2, it is possible to carry out a treatment, for example, by inserting the snare sheath SS into the first treatment tool insertion channel CH1 and by inserting another treatment tool into the second treatment tool insertion channel CH2.

A hooked portion 42 is formed such that it intersects with a center axis C3 of the first treatment tool insertion channel CH1, that it does not intersect with a center axis C4 of the second treatment tool insertion channel CH2, and that it is extended radially inwardly. Therefore, even when the cap portion 41 is fitted over the insertion section I2 of the endoscope E2, it is possible for a treatment tool that is inserted in the second treatment tool insertion channel CH2 to protrude from a tip end aperture plane 41a of the cap portion 41 toward the tip side.

Next, a description will be given of an operation of the endoscope hood 40 according to the fourth embodiment of the present invention.

Firstly, the fitting portion 7 of the endoscope hood 40 is fitted over the tip of the insertion section I2 of the endoscope E2, and then, the thus-fitted insertion section I2 is inserted in a body cavity such that the tip end aperture plane 41a of the cap portion 41 is disposed in the vicinity of a mucosa portion to be cut or excised.

Subsequently, the snare sheath SS is inserted into the first treatment tool insertion channel CH1 such that the tip thereof protrudes within the cap portion 41. Then, an unillustrated slider is forwardly moved toward the tip side with respect to the control portion main body such that the folded-back portion W of the snare wire SW is projected from the snare sheath SS. At this time, the folded-back portion W abuts against the hooked portion 42 and then engages the auxiliary hooked portion 8. Thereafter, the snare wire SW is radially and circumferentially extended along the hooked portion 42 under a principle similar to that of the first embodiment.

While injecting a physiological saline solution by the use of the injection needle NE, the injection needle NE is projected in the cap portion 41 through the second treatment tool insertion channel CH2. At this time, the injection needle NE is not hooked at the hooked portion 42 and the auxiliary hooked portion 8, but it protrudes through the tip end aperture plane 41a to thereby puncture a mucous membrane.

In this way, after the swelling operation in which a physiological saline solution is injected has been completed, the suction operation is carried out by the use of the second treatment tool insertion channel CH2 to raise or protrude the mucous membrane and then the binding and energizing operation is carried out by the use of the snare wire that has been extended or by the use of the loop thereof that has been expanded or widened.

With this endoscope hood 40 in which the flexible tube 6 is not provided and which is simply fitted over the insertion section I2 of the endoscope E2 with the two channels provided therein, it is possible to obtain an operation and effects which are similar to those of the first embodiment.

Figure 16:
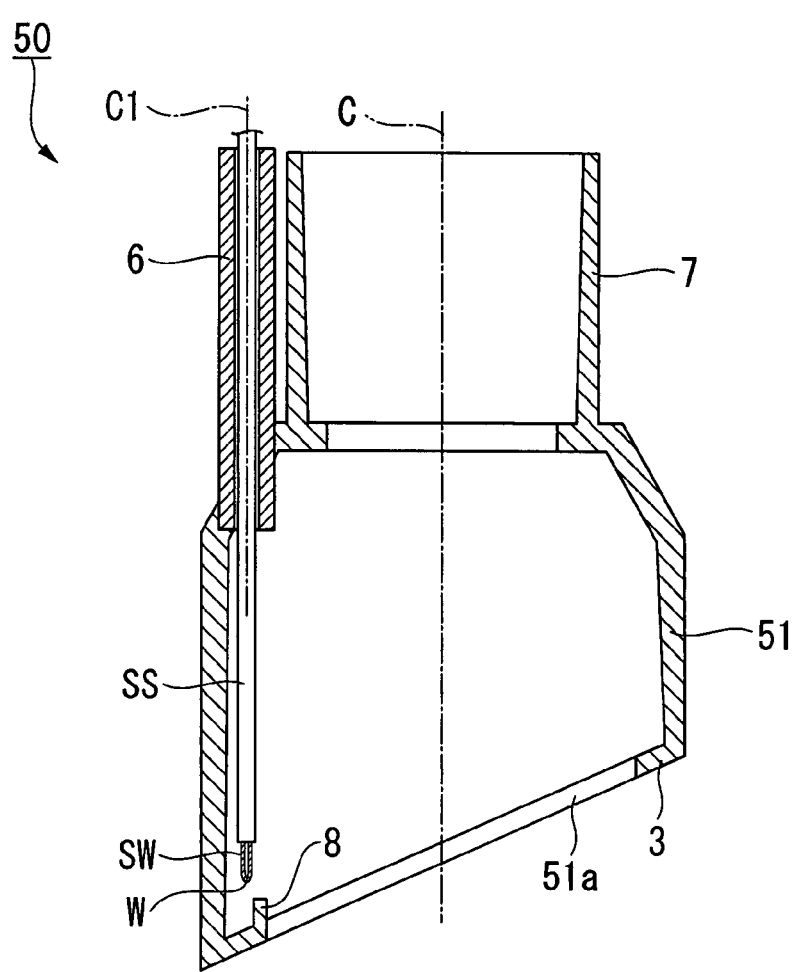
FIG. 16 is a cross-sectional view illustrating a main portion of an endoscope hood according to a fifth embodiment of the present invention.
Figure 17:
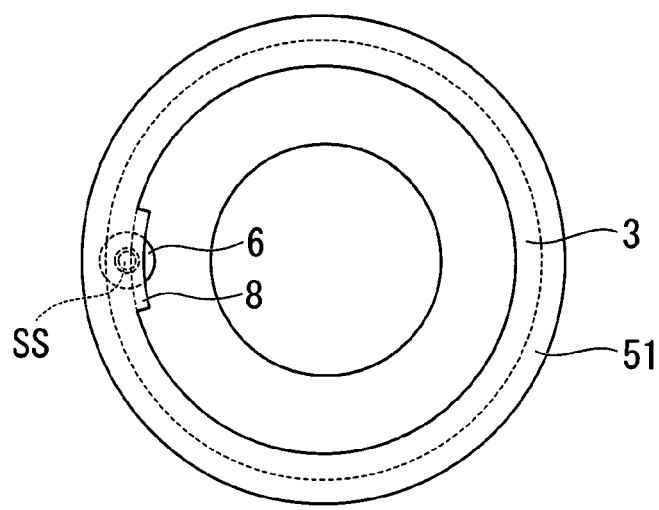
FIG. 17 is a plan view of the endoscope hood according to the fifth embodiment of the present invention.

Next, with reference to FIGS. 16 and 17, a description will be given of a fifth embodiment of the present invention.

Note that components which are the same or equivalent as those of the above-mentioned first to fourth embodiments are assigned the same reference numerals and that duplicate descriptions are appropriately omitted.

The fifth embodiment is different from the first embodiment in that a cap portion 51 of an endoscope hood 50 according to the fifth embodiment includes a tip end aperture plane 51a that is formed and slanted at a predetermined angle with respect to the center axis C of the cap portion 51 such that the length from the proximal end of the cap portion 51 to an intersecting point between the tip end aperture plane 51a and the center axis C1 of the flexible tube 6 is longer than any other corresponding length.

Since a side surface of the cap portion 51 forms an acute angle with the hooked portion 3 in the vicinity of the intersecting point described above, during the extension of the snare wire SW in the cap portion 51, it is possible to more preferably turn the snare wire SW toward the proximal end side of the cap portion 51 and then more appropriately extend the snare wire SW along the hooked portion 3, as compared to the first embodiment. Therefore, as compared to the endoscope hood 1 according to the first embodiment, it is possible to more effectively prevent the snare wire SW from departing from the hooked portion 3 once the snare wire SW is put in position along the hooked portion 3.

Figure 18:
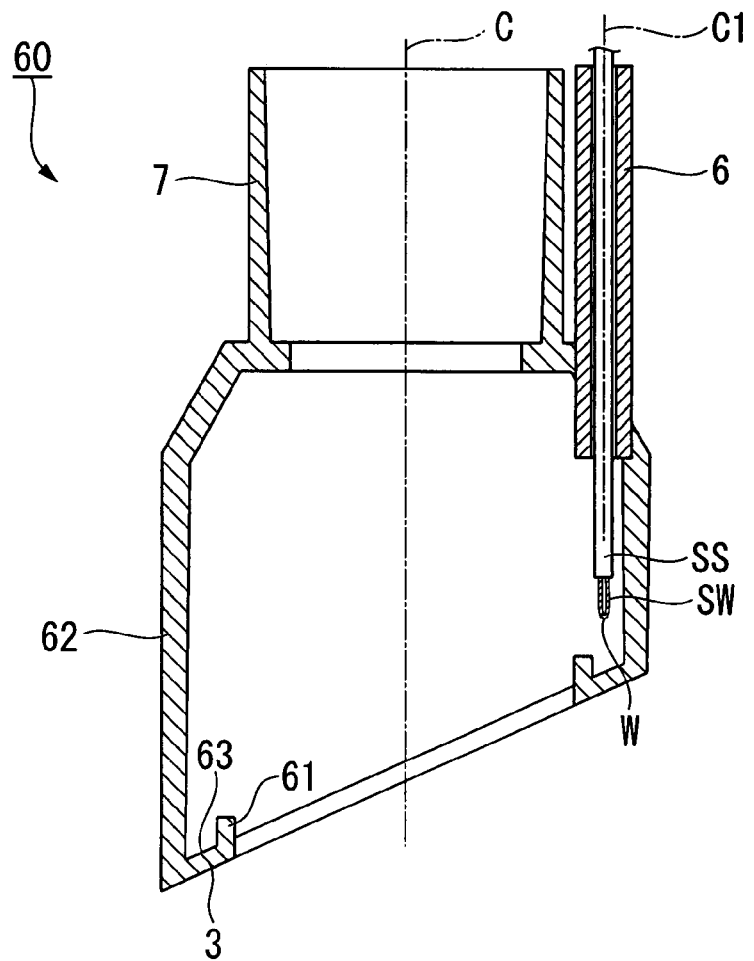
FIG. 18 is a cross-sectional view illustrating a main portion of an endoscope hood according to a sixth embodiment of the present invention.
Figure 19:
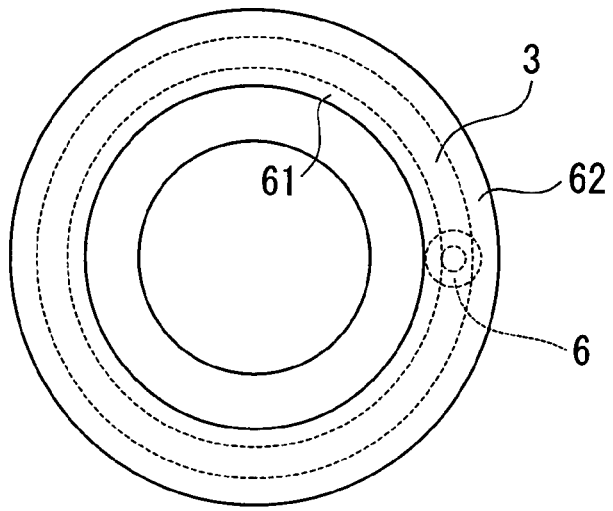
FIG. 19 is a plan view of the endoscope hood according to the sixth embodiment of the present invention.

Next, with reference to FIGS. 18 and 19, a description will be given of a sixth embodiment of the present invention.

Note that components which are the same or equivalent as those of the above-mentioned first to fifth embodiments are assigned the same reference numerals and that duplicate descriptions are appropriately omitted.

The sixth embodiment is different from the first embodiment in that an auxiliary hooked portion 61 of an endoscope hood 60 according to the sixth embodiment is not provided only in the vicinity of a position at which the hooked portion 3 and the center axis C1 of the flexible tube 6 intersect, but provided all around the circumference of hooked portion 3 and formed so as to bend at the internal edge of the hooked portion 3 and to extend toward the proximal end side of a cap portion 62

With this endoscope hood 60 in which a gutter or cradle 63 for receiving the snare wire SW is formed by the hooked portion 3, the auxiliary hooked portion 61 and an inner surface of the cap portion 62, it is possible to effectively prevent the snare wire SW from departing from the hooked portion 3 once the snare wire SW is extended in the cap portion 62 and put in position along the hooked portion 3.

Note that the technical scope of the present invention is not limited to the embodiments described above and that various modifications can be made without departing from the scope of the subject matter of the present invention.

Figure 20:
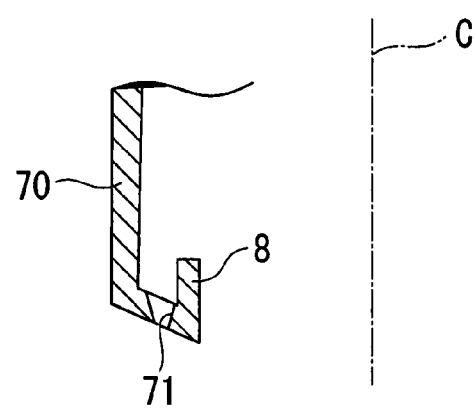
FIG. 20 is a partial cross-sectional view illustrating a modified example of the endoscope hood according to the third embodiment of present invention.

For example, although the locking portion 32 is provided with the through-hole 35 whose internal diameter is constant in the third embodiment, as illustrated in FIG. 20, a hooked portion 72 may be provided with a through-hole 71 whose internal diameter is gradually decreased in accordance with the approaching the tip side of a cap portion 70. With this structure, it is possible to appropriately prevent the snare wire SW from breaking through the through-hole 71.

Figure 21:
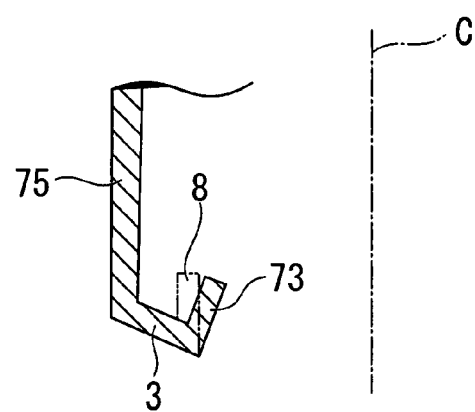
FIG. 21 is a partial cross-sectional view illustrating a modified example of the endoscope hood according to the first embodiment of present invention.

Further, as illustrated in FIG. 21, an auxiliary hooked portion 73 may be formed so as to be curved and extended toward the proximal end side of a cap portion 75 with an inclination toward the center axis C. With this structure, when the snare wire is radially extended, it is possible to firmly catch or hook the snare wire by the auxiliary hooked portion 73.

Figure 22:
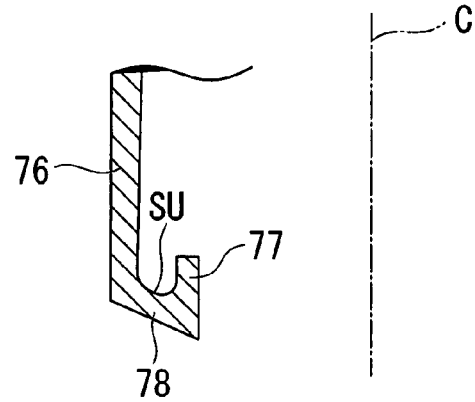
FIG. 22 is a partial cross-sectional view illustrating a further modified example of the endoscope hood according to the first embodiment of present invention.

Further, as illustrated in FIG. 22, in a cross-sectional plane containing the center axis C of a cap portion 76, an auxiliary hooked portion 77, a hooked portion 78 connected to the auxiliary hooked portion 77, and an inner surface of the cap portion 76 may form a continuous line SU curved with substantially the same center of curvature. With this structure, it is possible to firmly catch or hook a folded-back portion of the snare wire.

Figure 23:
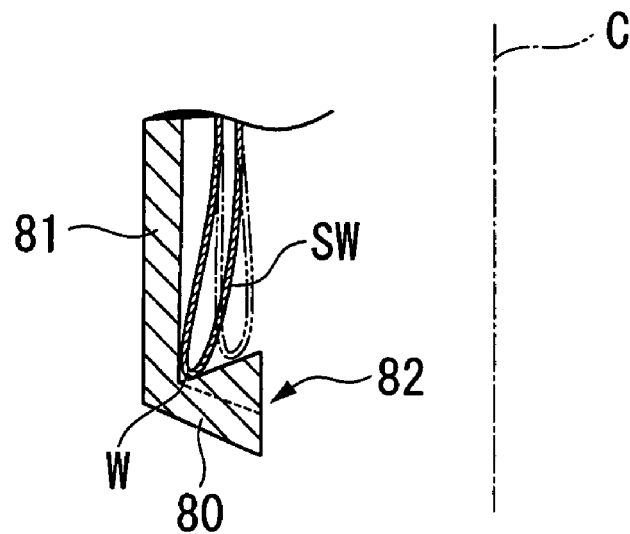
FIG. 23 is a partial cross-sectional view illustrating a yet further modified example of the endoscope hood according to the first embodiment of present invention.

Further, as illustrated in FIG. 23, a hooked portion 80 may be formed with a locking portion 82 such that the thickness thereof along the center axis C is gradually increased in accordance with the approaching the center axis. With this structure, it is possible to firmly catch or hook the folded-back portion W of the snare wire SW since the folded-back portion W is radially outwardly biased when it comes in contact with a locking portion 82.

Figure 24:
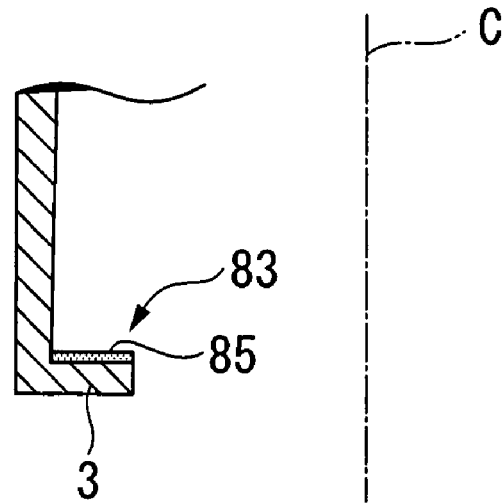
FIG. 24 is a partial cross-sectional view illustrating a still further modified example of the endoscope hood according to the first embodiment of present invention.

Further, as illustrated in FIG. 24, a locking portion 83 may be formed on a portion, or throughout the circumference, of a top surface of the hooked portion 3 and provided with a friction generating portion 85 which has a larger coefficient of friction than that of the top surface of the hooked portion 3. With this structure, it is possible to catch or hook the folded-back portion W such that the snare wire can be turned upside-down therearound due to high friction force generated when the folded-back portion W of the snare wire abuts against the friction generating portion 85.

Figure 25:
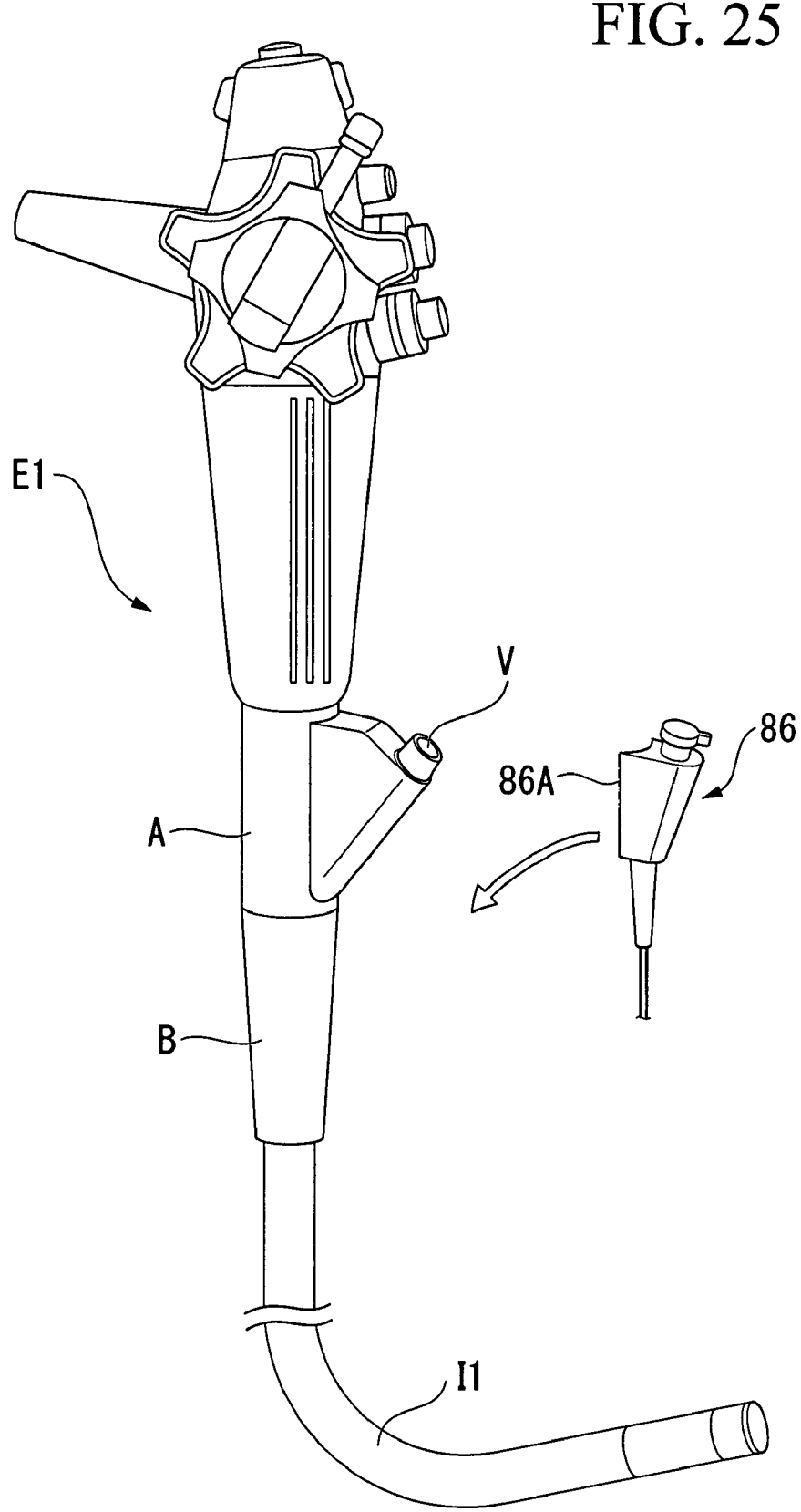
FIG. 25 is a partial cross-sectional view illustrating a different modified example of the endoscope hood according to the first embodiment of present invention.

Furthermore, instead of disposing the hook hole 10A into which the forceps opening V is insertable, as illustrated in FIG. 25, an attachment 86 may be provided which has an attaching surface 86A through which it is detachably attachable anywhere to a bending prevention section B or in the vicinity of a control portion A near the forceps opening V of the endoscope E1. With this structure, when detached, the attachment 86 is not an obstruction that blocks the operation related to the forceps opening V.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. An endoscopic treatment instrument comprising:
    a cylinder adapted to be fitted over a tip of an insertion section of an endoscope;
    a loop-shaped snare wire which protrudes in the cylinder from a snare sheath that is extendable and retractable with respect to the insertion section and which is extendable within the cylinder;
    a hooked portion which is radially inwardly extended from the circumference of a tip of the cylinder and which holds the snare wire within the cylinder;
    a locking portion provided on the hooked portion in front of a distal end of the snare wire and the snare sheath so as to face the distal end of the snare wire and the snare sheath; and
    an auxiliary hooked portion bent at an end part of the hooked portion and extending toward the proximal end of a cap portion, wherein
    when the snare wire advances to the locking portion, the locking portion contacts a folded-back portion of the snare wire and the locking portion and the auxiliary hooked portion holds the folded-back portion.

2. The endoscopic treatment instrument as recited in claim 1, wherein the auxiliary hooked portion protrudes from an end portion of the hooked portion in the vicinity of a point where the extension of the snare wire intersects toward a base end side of the cylinder.

3. The endoscopic treatment instrument as recited in claim 1, wherein the locking portion includes a depressed portion or through-hole which is provided on the hooked portion in the vicinity of which the extension of the snare wire intersects.

4. The endoscopic treatment instrument as recited in claim 1, wherein the locking portion includes a friction generating portion which is provided on an outer surface of the hooked portion and which has a larger coefficient of friction than the outer surface of the hooked portion.

5. The endoscopic treatment instrument as recited in any one of claims 1, 2 and 3, further comprising a tube which opens at its tip in the cylinder and in which the snare sheath is received so as to be extendable and retractable.

* * * * *